United States Patent [19]

Denzel et al.

[11] 4,072,680
[45] Feb. 7, 1978

[54] DERIVATIVES OF PYRAZOLO[1,5-a]PYRIDO[3,2-e]PYRIMIDINE

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 791,814

[22] Filed: Apr. 28, 1977

[51] Int. Cl.$^2$ .................. C07D 471/14; A61K 31/415
[52] U.S. Cl. ..................... 260/256.4 F; 260/256.5 R; 424/251
[58] Field of Search .................... 260/256.4 F, 256.5 R

[56] References Cited

U.S. PATENT DOCUMENTS

| | | | |
|---|---|---|---|
| 3,045,015 | 7/1962 | Miller et al. | 260/256.4 F |
| 3,313,815 | 4/1967 | Wolfe et al. | 260/256.4 F |
| 3,329,679 | 7/1967 | Sulkowski et al. | 260/256.4 F |
| 3,894,021 | 7/1975 | Denzel et al. | 260/256.4 F |

OTHER PUBLICATIONS

Checchi, "Chemical Abstracts," vol. 53, 1959, Cols. 21974b–21975g.

*Primary Examiner*—Paul M. Coughlan, Jr.
*Assistant Examiner*—James H. Turnipseed
*Attorney, Agent, or Firm*—Lawrence S. Levinson; Merle J. Smith

[57] ABSTRACT

New derivatives of pyrazolo[1,5-a]pyrido[3,2-e]pyrimidine have the general formula

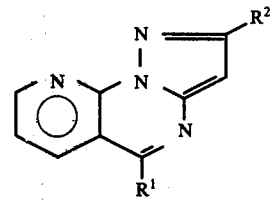

The new compounds are useful as anti-inflammatory agents.

16 Claims, No Drawings

DERIVATIVES OF PYRAZOLO[1,5-A]PYRIDO[3,2-E]PYRIMIDINE

SUMMARY OF THE INVENTION

This invention relates to new derivatives of pyrazolo[1,5-a]pyrido[3,2-e]pyrimidine. These new compounds have the general formula

[Structure I]

The symbols have the following meanings in formula I and throughout this specification:
$R^1$ is lower alkoxy, lower alkylthio, amino, lower alkylamino or di(lower alkyl)amino.
$R^2$ is hydrogen or lower alkyl.

REFERENCE TO RELATED APPLICATIONS

Reference is made to our copending applications Ser. No. 630,120, filed Nov. 7, 1975 now U.S. Pat. No. 4,026,893, and 746,676 and 764,677, both filed Feb. 2, 1977 which relate to pyrazolo[1,5-a]pyrido[3,2-e]pyrimidine-7-carboxylic acid derivatives.

DETAILED DESCRIPTION OF THE INVENTION

The lower alkyl groups are straight or branched chain hydrocarbon groups having up to seven carbon atoms in the chain, e.g., methyl, ethyl, propyl, isopropyl, butyl, isobutyl, t-butyl, amyl, hexyl, heptyl, etc. The $C_1$-$C_4$ lower alkyl groups and especially $C_1$-$C_2$ groups are preferred.

The lower alkoxy and lower alkylthio groups are similar, including lower alkyl groups of the kind described above attached to oxygen or sulfur, respectively. The $C_1$-$C_4$ groups similarly constitute preferred and especially preferred groups, respectively. They include, for example, methoxy, ethoxy, propoxy, isopropoxy, butoxy, isobutoxy, t-butoxy, methylthio, ethylthio, propylthio and the like.

The amino, lower alkylamino and di(lower alkyl)amino groups are basic groups which correspond to the formula $$-N\begin{matrix}R^3\\R^4\end{matrix}$$

$R^3$ and $R^4$ each being hydrogen or lower alkyl. These include, for example, amino, methylamino, ethylamino, propylamino, dimethylamino, diethylamino, methylethylamino, dipropylamino, and the like.

The products of the Examples are preferred embodiments.

Especially preferred compounds of formula I are those wherein
$R^1$ is lower alkoxy (especially $C_2$-$C_4$-lower alkoxy), lower alkylthio (especially $C_1$-$C_2$-lower alkylthio) or di(lower alkyl)amino (especially di($C_1$-$C_4$-lower alkyl)amino);
$R^2$ is hydrogen or lower alkyl, especially methyl.

The new compounds of formula I are formed by the following series of reactions. The symbols in the structural formulas have the same meaning as previously described.

A 2-halonicotinic acid halide of the formula

[Structure II]

wherein hal represents a halogen, preferably chlorine, is made to react with a 5-aminopyrazole of the formula

[Structure III]

The reaction is accomplished in a solvent like dioxane, diethyl ether or the like and in the presence of a base, e.g., a trialkylamine like trimethylamine. By this procedure, a compound of the formula

[Structure IV]

is formed. This compound is cyclized in an inert organic solvent like diphenyl ether by heating at about 220°-240° C forming a compound of the formula

[Structure V]

which is now halogenated by treating with an inorganic acid halide, preferably an acid chloride like phosphorus oxychloride, resulting in the formation of a compound of the formula

[Structure VI]

Compounds of formula I, wherein $R^1$ is a lower alkoxy or lower alkylthio group are now produced by reaction of the compound of formula VI with the alkali metal alkoxide or alkali metal mercaptide containing the desired lower alkyl group (which can be formed in situ).

Compounds of formula I wherein $R^1$ is an amino group are prepared by reaction of a compound of formula VI with an amine of the formula

wherein $R^3$ and $R^4$ each is hydrogen or lower alkyl.

Additional experimental details are found in the examples.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally or parenterally in dosages of about 5 to 50 mg/kg/day, preferably 5 to 25 mg/kg/day, in single or 2 to 4 divided doses, as indicated by the carageenan edema assay in rats or delayed hypersensitivity skin reaction test.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

For topical administration as an anti-inflammatory agent, a conventional lotion, ointment, or cream containing about 0.1 to 3 percent by weight of a compound of formula I is formulated.

The following examples are illustrative of the invention and constitute preferred embodiments. They also serve as models for the preparation of other members of the group which can be produced by suitable substitution of starting materials. All temperatures are in degrees celsius.

EXAMPLE 1

5-Ethoxypyrazolo[1,5-a]pyrido[3,2-e]pyrimidine (a)

2-Chloro-N-(1H-pyrazol-5-yl)-3-pyridinecarboxamide 175 g. of 2-chloro-3-pyridinecarboxylic acid chloride are dissolved in 750 ml. of anhydrous dioxane containing 110 g. of triethylamine. At 10°, 83 g. of 5-aminopyrazole dissolved in 100 ml. of dioxane are added dropwise with stirring. After the addition is completed, the mixture is stirred overnight at room temperature, filtered and the precipitate washed with dioxane. The solvent is removed in vacuo and the oily residue crystallized with ethyl acetate. The product, 2-chloro-N-(1H-pyrazol-5-yl)-3-pyridinecarboxamide, is recrystallized from ethyl acetate, yield: 103 g. (46%); m.p. 162.8°.

(b) 5-Hydroxypyrazolo[1,5-a]pyrido[3,2-e]pyrimidine 103 g. of 2-chloro-N-(1H-pyrazol-5-yl)-3-pyridinecarboxamide are suspended in 600 ml. of diphenyl ether and heated with stirring at 180° until the evolution of HCl gas ceases. After cooling to room temperature, 5-hydroxypyrazolo[1,5-a]pyrido[3,2-e]pyrimidine is filtered off, yield: 75 g. (88%); m.p. ≧ 300° (DMF).

(c) 5-Chloropyrazolo[1,5-a]pyrido[3,2-e]pyrimidine 75 g. of hydroxypyrazolo[1,5-a]pyrido[3,2-e]pyrimidine are refluxed in 200 ml. of phosphorus oxychloride for 12 hours with stirring. The excess phosphorus oxychloride is removed in vacuo and the remaining oil poured onto ice. The aqueous solution is neutralized with sodium hydroxide and evaporated in vacuo to about 100 ml. The product, 5-chloropyrazolo[1,5-a]pyrido[3,2-e]pyrimidine, crystallizes and is filtered off, yield: 60 g. (73%); m.p. 159.8° (ethyl acetate).

(d) 5-Ethoxypyrazolo[1,5-a]pyrido[3,2-e]pyrimidine 2.04 g. of 5-chloropyrazolo[1,5-a]pyrido[3,2-e]pyrimidine are added to a solution of 0.3 g. sodium in 20 ml. dry alcohol. The solution is refluxed for 1 hour. After the addition of 20 ml. of water, 5-ethoxypyrazolo[1,5-a]pyrido-[3,2-e]pyrimidine precipitates and is filtered off, yield: 1.6 g. (79%); m.p. 161.8° (ethyl acetate).

EXAMPLE 2

5-Butoxypyrazolo[1,5-a]pyrido[3,2-e]pyrimidine 2.04 g. of 5-chloropyrazolo[1,5-pyrido[3,2-e]pyrimidine are added to a solution of 0.3 g. sodium in 20 ml. of butyl alcohol and the solution is refluxed for 5 hours with stirring. The solvent is distilled off and the residue extracted with hot ligroin. The product, 5-butoxypyrazolo-[1,5-a]pyrido[3,2-e]pyrimidine, crystallizes on standing, yield: 1.8 g. (75%); m.p. 99.8°.

EXAMPLE 3

5-Methoxypyrazolo[1,5-a]pyrido[3,2-e]pyrimidine

By substituting ethyl alcohol for methyl alcohol in the procedure of Example 1d, 5-methoxypyrazolo[1,5-a]pyrido[3,2-e]pyrimidine is obtained, yield: 79%; m.p. 154.5° (ethyl acetate).

EXAMPLE 4

N,N-Diethylpyrazolo[1,5-a]pyrido[3,2-e]pyrimidin-5-amine 2.04 g. of 5-chloropyrazolo[1,5-a]pyrido[3,2-e]pyrimidine of Example 1c are added to 20 ml. of diethylamine. The solution is refluxed for 5 hours. The excess diethylamine is distilled off and the residue is treated with 5 ml. water and extracted three times with 10 ml. portions of ethyl acetate. The organic layers are combined, dried over sodium sulfate, filtered and evaporated to dryness. The residual N,N-diethylpyrazolo[1,5-a]pyrido[3,2-e]pyrimidin-5-amine is recrystallized from ethyl acetate/petroleum ether, yield: 2 g. (83%); m.p. 102°.

EXAMPLE 5

5-(Methylthio)pyrazolo[1,5-a]pyrido[3,2-e]pyrimidine 2.04 g. of 5-chloropyrazolo[1,5-a]pyrido[3,2-e]pyrimidine are suspended in 20 ml. of dry dimethylformamide. 1.5 g. of sodium methylmercaptide are added and the mixture is stirred at 60° for 10 hours. The solvent is removed in vacuo and 10 ml. of water are added to the residue. Crystalline 5-(methylthio)-pyrazolo[1,5-a]pyrido[3,2-e]pyrimidine is filtered off and recrystallized from ethyl acetate, yield: 1.9 g. (90%); m.p. 192°.

EXAMPLE 6

2-Methyl-5-(methylthio)pyrazolo[1,5-a]pyrido[3,2-e]pyrimidine (a)

5-Hydroxy-2-methylpyrazolo[1,5-a]pyrido[3,2-e]pyrimidine

By substituting for the 5-aminopyrazole in the procedure of Example 1a 5-amino-3-methylpyrazole, 2-chloro-N-(3-methyl-1H-pyrazol-5-yl)-3-pyridinecarboxamide is obtained. The product cannot be crystallized and is converted immediately to 5-hydroxy-2-methylpyrazolo[1,5-a]pyrido[3,2-e]pyrimidine, using the same procedure as given in Example 1b for 5-hydroxypyrazolo[1,5-a]pyrido[3,2-e]pyrimidine, yield: 76%; m.p. ≧ 300° (DMF).

(b)

5-Chloro-2-methylpyrazolo[1,5-a]pyrido[3,2-e]pyrimidine

By substituting for the 5-hydroxypyrazolo[1,5-a]pyrido-[3,2-e]pyrimidine in the procedure of Example 1c 5-hydroxy-2-methylpyrazolo[1,5-a]pyrido[3,2-e]pyrimidine of Example 6a, 5-chloro-2-methylpyrazolo[1,5-a]pyrido[3,2-e]pyrimidine is obtained, yield: 65%; m.p. 202.2°.

(c)

2-Methyl-5-(methylthio)pyrazolo[1,5-a]pyrido[3,2-e]pyrimidine

By replacing the 5-chloropyrazolo[1,5-a]pyrido[3,2-e]-pyrimidine with 5-chloro-2-methylpyrazolo[1,5-a]-pyrido[3,2-e]pyrimidine in the procedure of Example 5, 2-methyl-5-(methylthio)pyrazolo[1,5-a]pyrido[3,2-e]pyrimidine is obtained, yield: 85%; m.p. 189.9° (ethyl acetate).

EXAMPLE 7

N-Propylpyrazolo[1,5-a]pyrido[3,2-e]pyrimidin-5-amine

By substituting n-propylamine for the diethylamine in the procedure of Example 4, N-propylpyrazolo[1,5-a]-pyrido[3,2-e]pyrimidin-5-amine is obtained.

EXAMPLE 8

Pyrazolo[1,5-a]pyrido[3,2-e]pyrimidin-5-amine

By substituting ammonia for the diethylamine in the procedure of Example 4, pyrazolo[1,5-a]pyrido[3,2-e]pyrimidin-5-amine is obtained.

EXAMPLE 9

N-Methylpyrazolo[1,5-a]pyrido[3,2-e]pyrimidin-5-amine

By substituting methylamine for the diethylamine in the procedure of Example 4, N-methylpyrazolo[1,5-a]pyrido[3,2-e]-pyrimidin-5-amine is obtained.

What is claimed is:
1. A compound of the formula

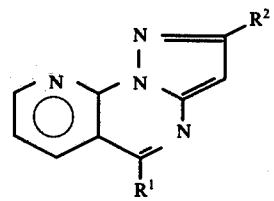

wherein $R^1$ is lower alkoxy, lower alkylthio, amino, lower alkylamino or di(lower alkyl)amino;
$R^2$ is hydrogen or lower alkyl.

2. A compound as in claim 1 wherein $R^1$ is lower alkoxy.

3. A compound as in claim 1 wherein $R^1$ is lower alkylthio.

4. A compound as in claim 1 wherein $R^1$ is amino.

5. A compound as in claim 1 wherein $R^1$ is lower alkylamino.

6. A compound as in claim 1 wherein $R^1$ is di(lower alkyl)amino.

7. A compound as in claim 1 wherein $R^1$ is lower alkoxy, lower alkylthio or di(lower alkyl)amino and $R^2$ is hydrogen or lower alkyl.

8. A compound as in claim 2 wherein $R^2$ is hydrogen.

9. A compound as in claim 3 wherein $R^2$ is hydrogen.

10. A compound as in claim 6 wherein $R^2$ is hydrogen.

11. A compound as in claim 1 wherein $R^1$ is ethoxy and $R^2$ is hydrogen.

12. A compound as in claim 1 wherein $R^1$ is butoxy and $R^2$ is hydrogen.

13. A compound as in claim 1 wherein $R^1$ is methoxy and $R^2$ is hydrogen.

14. A compound as in claim 1 wherein $R^1$ is diethylamino and $R^2$ is hydrogen.

15. A compound as in claim 1 wherein $R^1$ is methylthio and $R^2$ is hydrogen.

16. A compound as in claim 1 wherein $R^1$ is methylthio and $R^2$ is methyl.

* * * * *